(12) United States Patent
Hong et al.

(10) Patent No.: US 6,296,878 B1
(45) Date of Patent: Oct. 2, 2001

(54) TORTOISE OIL, TURTLE OIL, COMPOSITIONS CONTAINING THEM, THEIR PREPARATION PROCESSES AND USES

(75) Inventors: Mengxue Hong; Shanshan Zhong; Rulian Bian, all of Zhejiang (CN)

(73) Assignee: Hainan Life Nourishing Pharmacy Co., Ltd., Haikou (CN)

( * ) Notice: Subject to any disclaimer, the term of this patent is extended or adjusted under 35 U.S.C. 154(b) by 0 days.

(21) Appl. No.: 09/297,425
(22) PCT Filed: Oct. 20, 1997
(86) PCT No.: PCT/CN97/00103
　§ 371 Date: Jun. 28, 1999
　§ 102(e) Date: Jun. 28, 1999
(87) PCT Pub. No.: WO98/18478
　PCT Pub. Date: May 7, 1998

(30) Foreign Application Priority Data

Oct. 30, 1996 (CN) ............................................. 96120430

(51) Int. Cl.⁷ ................................................... A61K 35/12
(52) U.S. Cl. ................ 424/522; 424/400; 424/401; 424/439; 424/451; 424/520; 424/455
(58) Field of Search ................................ 424/400, 401, 424/59, 60, 450, 451, 455, 439, 520, 522, 523

(56) References Cited

U.S. PATENT DOCUMENTS 5,866,160　2/1999　Hong et al. ........................... 424/451

FOREIGN PATENT DOCUMENTS

| 1 091 311 | 8/1994 | (CN) . |
|---|---|---|
| 1 098 604 | 2/1995 | (CN) . |
| 1 132 090 | 10/1996 | (CN) . |
| 61 134322 | 6/1986 | (JP) . |
| 62-172097 | 7/1987 | (JP) . |
| 63-310806 | 12/1988 | (JP) . |
| 5-186328 | 7/1993 | (JP) . |
| 7-157421 | 6/1995 | (JP) . |
| WO 95/18625 | 7/1995 | (WO) . |

OTHER PUBLICATIONS

Turdyev, A.A., et al., "Therapeutic effect of purified compounds of a tortoise spleen extract", Chemical Abstracts, vol. 106, No. 1, 1987, p. 231.

Database EPODOC Online!, XP002142718, *abstract*, & CN 1 095 292 A (Wang Jie), Nov. 23, 1994.

Database EPODOC Online!, XP002142719, *abstract*, & CN 1 088 098 A (Zhu Shengtian), Jun. 22, 1994.

Primary Examiner—Dameron L. Jones
(74) Attorney, Agent, or Firm—Christie, Parker & Hale, LLP

(57) ABSTRACT

The present invention relates to tortoise oil, turtle oil, compositions thereof and their uses.

19 Claims, No Drawings

TORTOISE OIL, TURTLE OIL, COMPOSITIONS CONTAINING THEM, THEIR PREPARATION PROCESSES AND USES

This application is a 371 of PCT/CN97/00103 filed Oct. 20, 1997.

FIELD OF THE INVENTION

The present invention relates to the tortoise oil, turtle oil, composition containing them, their preparation processes and their uses.

BACKGROUND OF THE INVENTION

Both tortoise and turtle are animals which show tonic actions on the human body. In general, the use of both animals is considered as dairy food through cooking. In recent years people process them by chemical and physical methods to form oral liquid or capsules in solid-form for the application. However, both tortoise oil and turtle oil as byproducts during possessing are neglected. Therefore no report or information on the usage of tortoise oil and turtle oil are found before the present invention is completed.

The object of the invention lies in developing the extensive value of tortoise oil and turtle oil through the research on uses thereof.

SUMMARY OF THE INVENTION

Researching widely and going deep into the work, the inventor unexpectedly discovered that tortoise oil, turtle oil and compositions containing them are valuable for use on the human body, for example, for anti-inflammatory and anti-itching action, prevention and/or treatment of disorders of the cardiovascular system, protective action against sunlight (ultraviolet ray) radiation, analgesic action, promotive action on proliferation of human fibroblasts, therapeutic effect on fire burn and/or scald, therapeutic effect on psoriasis as well as use in cosmetics. The present invention is completed on the basis of the above-mentioned discovery.

The first object of the present invention relates to tortoise oil and turtle oil with the following physical and chemical constants:

| Physical and chemical constants | Tortoise oil | Turtle oil |
|---|---|---|
| Relative density | 0.9159 | 0.9184 |
| Refractive index | 1.4690 | 1.4708 |
| Melting point (° C.) | 24–33 | 25–38 |
| Melting point of fatty acid (° C.) | 31 | 32.9 |
| Acid value | 3.4 | 2.09 |
| Saponification-number (value) | 202.22 | 199.99 |
| Hydroxyl value | 5.38 | 8.78 |
| Iodine value | 3.16 | 2.64 |
| Total amount of fat (%) | 92.14 | 80.49 |
| Saturated fatty acids (mg/g) | | |
| Lauric acid ($C_{12}$:0) | 1.23 | 0.76 |
| Myristic acid ($C_{14}$:0) | 19.53 | 13.39 |
| Palmitic acid ($C_{16}$:0) | 172.76 | 186.93 |
| Stearic acid ($C_{18}$:0) | 70.45 | 84.01 |
| Unsaturated fatty acids | | |
| Tetradecenic acid ($C_{14}$:1) | | 1.44 |
| Palmitoleic acid ($C_{16}$:1) | 102.55 | 87.78 |
| Oleinic acid ($C_{18}$:1) | 430.12 | 336.59 |
| Linoleic acid ($C_{18}$:2) | 15.01 | 90.57 |
| Linolenic acid ($C_{18}$:3) | 13.09 | 36.49 |

In addition, a certain amount of eicosapentaenoic acid (EPA) and docosahexaenoic acid (DHA) etc. are found in tortoise oil and turtle oil during the fatty acid determination.

The present invention relates to tortoise oil having anti-inflammatory effect.

The present invention relates to tortoise oil having anti-itching effect.

The present invention relates to tortoise oil having analgesic effect.

The present invention relates to tortoise oil having preventive and/or therapeutic effect on disorders of the cardiovascular system.

The present invention relates to tortoise oil having therapeutic effect on psoriasis.

The present invention relates to turtle oil having anti-inflammatory effect.

The present invention related to turtle oil having anti-itching effect.

The present invention related to turtle oil having analgesic effect.

The present invention relates to turtle oil having preventive and/or therapeutic effect on disorders of the cardiovascular system.

The present invention relates to turtle oil having therapeutic effect on psoriasis.

The present invention relates to tortoise oil having protective action against sunlight (ultraviolet ray) radiation.

The present invention relates to tortoise oil promoting the proliferation of human fibroblasts.

The present invention relates to turtle oil having protective action against sunlight (ultraviolet ray) radiation.

The present invention relates to turtle oil promoting the proliferation of human fibroblasts.

The present invention relates to tortoise oil having therapeutic effect on fire burn and/or scald.

The present invention relates to turtle oil having therapeutic effect on fire burn and/or scald.

And also,

The present invention relates to compositions of tortoise oil and turtle oil.

The present invention relates to pharmaceutical compositions including tortoise oil and/or turtle oil, and excipients ordinarily used in the pharmaceutical field.

The present invention relates to cosmetics including tortoise oil and/or turtle oil, and additives or excipients ordinarily used in cosmetics.

The present invention relates to health food including tortoise oil and turtle oil, and suitable additives.

The present invention relates a method for preparing tortoise oil, comprising:

The fat taken from the internal organ of tortoise is decocted at 110–115° C. under the ordinary pressure to a complete melt, and the residual oil is removed by filtration. 20% fuller's earth is added to the clear oil, decoloring the mixture at 90° C. for 60 minutes, deodocozing the oil under vacuum (600 mg Hg) for not less than 90 min and meanwhile adding 0.02% vitamin E into the oil. The final product of tortoise oil with slight yellow color is obtained.

The fat taken from the internal organ of turtle is decocted at 110–115° C. under the ordinary pressure to a complete melt, and the residual oil is removed by filtration. 20% fuller's earth is added to the clear oil, decoloring the mixture at 90° C. for 60 minutes, deodocozing the oil under vacuum (600 mg Hg) for not less than 90 min, and meanwhile adding 0.02% vitamin E into the oil. The final product of turtle oil with slight yellow color is obtained.

The present invention relates also to a method for making a composition of tortoise oil and turtle oil comprising the step of mixing 0.01–99.99 by weight % tortoise oil with 99.99%–0.01 by weight % turtle oil.

The present invention also relates to a method for preparing the above-mentioned pharmaceutical composition, comprising mixing tortoise oil and/or turtle oil with an excipient ordinarily used in the pharmaceutical field.

The present invention also relates to a method for preparing the above-mentioned cosmetics comprising mixing tortoise oil and/or turtle oil with additives ordinarily used in cosmetics.

According to the present invention the products of tortoise oil and/or turtle oil of this invention are applicable to mammals including human beings.

According to the present invention the term "itching" of this invention indicates that cutaneous or mucous itching is reduced by physical factors (light, heat etc.), chemical factors and environmental factors (mosquito bite or insect sting).

DETAILED DESCRIPTION OF THE INVENTION

According to the present invention tortoise oil and/or turtle oil of this invention contain a great amount of saturated and unsaturated fatty acids. Therefore the products of tortoise oil and/or turtle oil can be used for preventing and/or treating disorders of the cardiovascular system of mankind as well as improving blood supply to the tissues and anti-senility, such as depressing blood-fat and blood viscosity, improving blood supply to the tissue and anti-oxidation.

According to the present invention the pharmaceutical composition of this invention can be made up by means known methods in this field as the following dosage forms, i.e. capsule, ointment, cream suspension, emulsion, plaster, suppository, percutaneous absorbent, sustained-release preparation, wherein the content of tortoise oil and/or turtle oil in these preparations must not be less than 0.1 weight %.

According to the present invention the cosmetics of this invention can be made up by means of known methods in this field as the following dosage forms, i.e. capsule, ointment, cream, suspension, emulsion, lotion, drop, whereto the content of tortoise oil and/or turtle oil must not be less than 0.01 weight %.

According to the present invention the health food of this invention can be made up by means of known methods of this field as capsule, wherein the content of tortoise oil and/or turtle oil must not be less than 0.01 weight %.

According to the present invention the tortoise oil, turtle oil, and compositions of tortoise oil and turtle oil of this invention, in pharmaceutical compositions, cosmetics, and health foods are taken by oral administration or local application.

According to the present invention the mentioned pharmaceutical compositions, cosmetics and health foods of this invention can be added with standard excipients or carriers suitable for preparing a variety of dosage forms, such as excipient, disintegrant, adhesive, coating, extender, lubricant, correctives, sweetening agent or auxiliary solvent etc. The excipients or carriers can be such as magnesium stearate, magnesium carbonate, kaolin, talc, lactose, mannitol, gelatin, starch, cellulose and its derivatives, polyethylene glycol, white vaseline, liquid paraffim, lauric acid oil and distilled water etc.

According to the present invention the tortoise oil, turtle oil and the tortoise oil and turtle oil compositions of this invention, in pharmaceutical composition of tortoise oil and/or turtle oil and cosmetics, as well as health foods containing tortoise oil and/or turtle oil, can be taken by oral administration or local application.

According to the present invention the tortoise oil and/or turtle oil of this invention must be taken in an amount not less than 0.01 weight %.

According to the present invention the amount of tortoise oil and/or turtle oil in the pharmaceutical composition of this invention must not be less than 0.1 weight %.

According to the present invention the amount of tortoise oil and/or turtle oil in the cosmetics of this invention must not be less than 0.01 weight %.

According to the present invention the cosmetics of this invention can be made up by means of known methods as the following dosage forms, such as ointments, creams and solutions.

In the following paragraphs the inventor will describe some biological experiments along with experimental examples and preparation examples as a further illustration for the present invention, but both of them could not be considered as any limitations to the present invention.

In addition, if there is no special explanation in the following biological experiments and examples, the percentage "%" indicates "weight %".

1. Anti-inflammatory Action

1. Xylene is smeared on the auricle of mice to induce acute inflammation with tumefaction.

The mice are treated with 0.5% tortoise oil, 0.5% turtle oil and 0.5% tortoise and turtle oil (mixture in half and half) respectively. The auricle tumefaction abates evidently. The rates of abatement of tumefaction show that the tortoise oil, turtle oil and combination of tortoise and turtle oil are 31.4%, 53.0% and 71.7% respectively. It means that all of three test samples have an evident anti-inflammatory action.

2. Carrageenin is injected to the hind leg of rat (plantar fascia) to induce inflammatory tumefaction on the plantar part. At 30 minutes before inflammation, 0.5% tortoise oil, 0.5% turtle oil and 0.5% combination of tortoise and turtle oil are smeared on the local part of planta respectively. All of three test samples have an evident protective action against inflammation. The rate of abatement of tumefaction show that the tortoise oil, turtle oil and combination of tortoise oil and turtle oil are 40.0%, 53.5% and 34% respectively. The anti-inflammatory action sustains for more than 5 hours.

Two above-mentioned experiments prove that 0.5% tortoise oil, 0.5% turtle oil and combination of 0.5% tortoise and turtle oil, i.e., all of three test samples, show an evident anti-inflammatory action sustaining for more than 5 hours. This kind of action may be applied to treat a variety of nonspecific inflammatory reactions of skin and mucosa by means of a local coating method.

2. Anti-itching Action

Histamine phosphate is injected into the planta pedis of guinea pig to induce itching. Itching threshold is determined, i.e. the threshold concentration which induces plantar itching and causes animals to lick their legs. And then 0.5% tortoise oil, 0.5% turtle oil and combination of 0.5% tortoise and turtle oil are smeared at the planta pedis respectively. The itching threshold (calculated as histamine mg/ml) is determined repeatedly. The experimental results prove that 0.5% tortoise oil, 0.5% turtle oil and 0.5% combination of tortoise and turtle oil, i.e., all three test samples, can obviously enhance the histamine-itching threshold. The rates of enhancement are 138.6%, 161.3% and 184.0% respectively. It is shown that all of them have an evident anti-pruritic action against histamine-induced itching. This function can be widely applied to treat a variety of local itching on skin or mucomembrane pruritus (itching) caused by chemical, physical (light and heat etc.) and environmental factors (mosquito bite or insect sting).

3. Protective Action Against Sunlight (Ultraviolet Ray) Radiation

Rats having an area of 40 $cm^2$ depilated are irradiated under a 30W UV lamp at a distance of 50 cm for 18 hours successively. The injuries appear as local spotty erythema, flake erythema, edema and desquamation. According to the degree of injury a mark is given to each test sample. The animals are smeared in advance with 0.5% tortoise oil, 0.5% turtle oil and 0.5% combination of tortoise and turtle oil. All of three test samples can evidently reduce the injury by UV radiation. The rates of abatement of injury are 39.30%, 54.50% and 69.60% respectively.

The above-mentioned experimental results show that tortoise oil, turtle oil and combined tortoise and turtle oil have an evident protective (inhibitory) action against UV radiation. It also reflects that all of the have a preventative (inhibitory) function against sunburn, so they can be applied to protect the skin from adverse reaction caused by sunlight radiation.

4. Analgesic Action

1. Hot plate method for determining the pain threshold of mice. The planta of mice is smeared in advance with 0.5% tortoise oil, 0.5% turtle oil and 0.5% combination of tortoise oil and turtle oil respectively. The pain threshold of mice is determined. All three test samples can enhance the pain threshold. The rates of enhancement are 48.8%, 175.3% and 112.9% respectively. The experimental results prove that all of three test samples have analgesic action.

2. Algogenic method with hot water (55° C.) for observing the analgesic effect. Mice tails are soaked in hot water. The latent period of tail retraction is defined as pain threshold. 0.5% tortoise oil, 0.5% turtle oil and 0.5% combination of tortoise oil and turtle oil are smeared on the mice tails respectively. Time of tail retraction is determined. All three test samples can prolong the tail retraction time, i.e. evident enhancement of pain threshold. The rates of enhancement are 46.4%, 132.2% and 282.2% respectively.

The above-mentioned experiments prove that tortoise oil, turtle oil and the combined tortoise oil and turtle oil have analgesic action. The action of turtle oil is stronger than that of tortoise oil. The action of the combined tortoise oil and turtle oil is stronger than that of a single one. This fact has provided a scientific basis that tortoise oil, turtle oil and combined tortoise oil and turtle oil can be used as an analgesic for treating local wound and ulcer.

5. Promotive Action on Proliferation of Human Fibroblast

The culture of human fibroblast in vitro by adding tortoise oil, turtle oil and combined tortoise oil and turtle oil is promoted. It is found that the cells proliferate quickly and the number of cells increase nearly by times. The concentration of tortoise oil and/or turtle oil for cell proliferation is 3.125~6.25 ug/ml. When the concentration arrives at 12.5 ug/ml, the value of cell proliferation is the biggest. The photos are being analyzed in order to make clear the reaction link for promoting the cell proliferation.

So far as medical use is concerned, it is advantageous to promote wound healing; as cosmetic use, to promote metabolism and proliferation of epidemic cells and to prevent skin from senility.

6. Distinct Therapeutic Effect on Second-Degree Scald on Rat

A model of second-degree scald by hot water is made on rat at 100% area of body surface and then 0.5% tortoise oil, 0.5% turtle oil and 0.5% combination of tortoise and turtle oil are smeared respectively on the local scalded part every 8 hours for 20 days in all. According to healing rate of surface wounds and rate of decrustation, the therapeutic effects are assessed. The results are as follows:

Influence on Decrustation Rate

| Groups | Decrustation rates (%) (x ± s) | | |
|---|---|---|---|
| | 10 days after scalding | 15 days | 20 days |
| Control | 8.0 ± 8.5 | 30.2 ± 6.7 | 58.0 ± 12.7 |
| Tortoise oil | 31.6 ± 8.3** | 84.0 ± 6.8** | 91.5 ± 7.1** |
| Turtle oil | 8.1 ± 1.7 | 65.0 ± 12.0** | 85.0 ± 10.0** |
| Combination of Tortoise and Turtle oil | 34.4 ± 7.0** | 88.1 ± 8.1** | 96.8 ± 5.0** |

Compared with the control **$P < 0.01$

Influence on Rate of Healing on Surface of Wound

| Group | Rate of healing on surface of wound (%) (x ± s) | | |
|---|---|---|---|
| | 10 days after scalding | 15 days | 20 days |
| Control | 6.1 ± 3.3 | 23.4 ± 5.1 | 53.6 ± 11.8 |
| Tortoise oil | 29.4 ± 16.2** | 74.8 ± 11.9** | 89.0 ± 16.9** |
| Turtle oil | 5.8 ± 2.4 | 55.0 ± 12.9** | 80.8 ± 13.6** |
| Composition of Tortoise oil and Turtle oil | 31.0 ± 12.6** | 76.6 ± 10.0** | 95.0 ± 2.7** |

Compared with the control **$P < 0.01$

Comparison of samples of surface wounds through pathologic sections is carried out. The experimental results prove that tortoise oil, turtle oil and combined tortoise oil and turtle oil, after being smeared on rat with second-degree scald, have an evident promotive effect on decrustation, decreasing local inflammation, promoting restoration and proliferation of epithelia, accelerating healing of surface of wound and obviously decreasing formation of scar. These therapeutic actions provide an experimental basis that the tortoise oil, turtle oil and combined tortoise oil and turtle oil can be applied to the treatment of burn and scald.

7. Therapeutic Action on Psoriasis

According to the published literature, 50% Ptmarol is smeared on guinea pig's skin of auricle once a day. A typical histological lesion which is similar to human psoriasis forms after 3 weeks, followed by incomplete cellular keratinization in the horny layer, distinct pigmentation, distinctly thick epiderm, increasing derreal papilla, ragged basilar membrane, transforming into prickle-cell layer mainly, karyopyknosis and necrosis of partial cells as well as leukocytic infiltration between cells.

After smearing 0.5% tortoise oil, 0.5% turtle oil and 0.5% combination of tortoise oil and turtle oil on test animals for treatment, the typical pathologic changes of psoriasis are evidently improved by these oils after 2 weeks. Epithelial keratinization is complete. Thickness of epithelial prickle-cell layer approaches a normal state. Leukocytic infiltration is decreased and its formation approaches a normal state.

EXAMPLE OF PREPARATION

According to the following prescription, the preparation of oil-in-water type containing tortoise oil and/or turtle oil is as follows:

| | |
|---|---|
| Hexadecanol | 120 g |
| Lauryl sodium sulfate | 10 g |
| White vaseline | 120 g |
| Nipagin A (ethylparaben) | 1 g |
| Glycerin | 50 ml |
| Tortoise oil and/or turtle oil | 5 g |
| Distilled water | q.s. |
| Total weight | 1000 g |

What is claimed is:

1. A composition of tortoise oil and turtle oil which comprises tortoise oil and turtle oil extracted from internal organ fat.

2. A pharmaceutical composition comprising tortoise oil and turtle oil, extracted from internal organ fat, and a pharmaceutical excipient.

3. A composition according to claim 1, which is formulated as one of a capsule and an oil solution.

4. A pharmaceutical composition according to claim 2, which is formulated as one of a capsule, ointment, cream, suspension, emulsion, plaster, suppository, percutaneous absorbent and sustained-release preparation.

5. A method for preparing the composition of claim 1, comprising the step of mixing 0.1–99.9% of tortoise oil with 0.1–99.9% of turtle oil.

6. A method for preparing the pharmaceutical composition of claim 2, comprising the step of mixing the tortoise oil and the turtle oil with an excipient.

7. A method of treating a disorder in a patient, the method comprising:

administering tortoise oil to the patient, wherein the disorder to be treated is selected from pain, a disorder of the cardiovascular system and psoriasis.

8. A method of treating a disorder in a patient, the method comprising:

administering turtle oil to the patient, wherein the disorder to be treated is selected from pain, a disorder of the cardiovascular system and psoriasis.

9. A method of treating or inhibiting damage to skin by ultraviolet light and promoting fibroblast proliferation, the method comprising administering tortoise oil to the skin.

10. A method of treating or inhibiting damage to skin by ultraviolet light and promoting fibroblast proliferation, the method comprising administering turtle oil to the skin.

11. A method of treating burns and scalds comprising administering tortoise oil to the burn or scald.

12. A method of treating burns and scalds comprising administering turtle oil to the burng or scald.

13. A method of preparing a composition comprising tortoise oil and turtle oil, the method comprising:

extracting the oil from fat taken from the internal organs of the tortoise and turtle, and combining the tortoise oil with the turtle oil.

14. The method of claim 13 further comprising adding at least one additional ingredient.

15. The method of claim 14 wherein the additional ingredient is vitamin E.

16. The method of claim 14 wherein the additional ingredient is an excipient.

17. The method of claim 14 wherein the additional ingredient is a cosmetic ingredient.

18. A method of preventing a disorder of the cardiovascular system in a patient, the method comprising administering tortoise oil to the patient.

19. A method of preventing a disorder of the cardiovascular system in a patient, the method comprising administering turtle oil to the patient.

* * * * *